United States Patent
Fischvogt

(10) Patent No.: US 9,320,861 B2
(45) Date of Patent: Apr. 26, 2016

(54) SMOKE VENT FOR ACCESS PORT DEVICE

(71) Applicant: Covidien LP, Mansfield, MA (US)

(72) Inventor: Gregory Fischvogt, Hamden, CT (US)

(73) Assignee: Covidien LP, Mansfield, MA (US)

( * ) Notice: Subject to any disclaimer, the term of this patent is extended or adjusted under 35 U.S.C. 154(b) by 118 days.

(21) Appl. No.: 14/158,267

(22) Filed: Jan. 17, 2014

(65) Prior Publication Data

US 2014/0235951 A1    Aug. 21, 2014

Related U.S. Application Data

(60) Provisional application No. 61/767,462, filed on Feb. 21, 2013.

(51) Int. Cl.
| | | |
|---|---|---|
| *A61B 17/02* | (2006.01) | |
| *A61M 13/00* | (2006.01) | |
| *A61B 17/34* | (2006.01) | |

(52) U.S. Cl.
CPC .......... *A61M 13/003* (2013.01); *A61B 17/3423* (2013.01); *A61B 17/3474* (2013.01); *A61B 2017/3429* (2013.01); *A61B 2218/008* (2013.01); *A61M 2202/0225* (2013.01); *A61M 2205/3334* (2013.01)

(58) Field of Classification Search
CPC ............... A61M 13/003; A61M 2202/0225; A61B 17/3423; A61B 17/3474; A61B 2017/3429; A61B 2218/008
USPC ............ 600/153, 156, 159, 206, 208; 604/27, 604/35, 45, 119, 540, 541
See application file for complete search history.

(56) References Cited

U.S. PATENT DOCUMENTS

| | | | |
|---|---|---|---|
| 4,735,603 | A | 4/1988 | Goodson et al. |
| 4,906,261 | A | 3/1990 | Mohajer |
| 4,963,134 | A | 10/1990 | Backscheider et al. |
| 4,986,839 | A | 1/1991 | Wertz et al. |
| 5,199,944 | A | 4/1993 | Cosmescu |
| 5,578,000 | A | 11/1996 | Greff et al. |
| 5,626,568 | A | 5/1997 | Yeh et al. |
| 5,674,219 | A | 10/1997 | Monson et al. |
| 5,688,256 | A | 11/1997 | Surratt et al. |
| 5,709,675 | A | 1/1998 | Williams |
| 5,836,301 | A | 11/1998 | Holian et al. |
| 5,910,291 | A | 6/1999 | Skalla et al. |
| 6,033,428 | A | 3/2000 | Sardella |
| 6,110,259 | A | 8/2000 | Schultz et al. |
| 6,589,316 | B1 | 7/2003 | Schultz et al. |
| 6,592,543 | B1 | 7/2003 | Wortrich et al. |

(Continued)

FOREIGN PATENT DOCUMENTS

| | | |
|---|---|---|
| WO | 01/91652 A1 | 12/2001 |
| WO | 2004/030547 A1 | 4/2004 |

*Primary Examiner* — Pedro Philogene
*Assistant Examiner* — David C Comstock

(57) ABSTRACT

An access port device is provided including a tubular member having a proximal end and a distal end with at least one lumen extending therethrough, a first ring secured at the proximal end of the tubular member, and a second ring secured at the distal end of the tubular member. The access port device further includes a flow regulator disposed on a top portion of the at least one lumen, the flow regulator having a head portion and a body portion, the body portion extending asymmetrically downward to form a substantially triangular opening for regulating an output rate of insufflation gasses from a surgical site.

19 Claims, 6 Drawing Sheets

(56) References Cited

U.S. PATENT DOCUMENTS

| | | |
|---|---|---|
| 6,663,610 B1 | 12/2003 | Thompson et al. |
| 7,207,977 B2 | 4/2007 | Thompson et al. |
| 7,258,712 B2 | 8/2007 | Schultz et al. |
| 7,959,698 B2 | 6/2011 | Schultz et al. |
| 8,414,550 B2 | 4/2013 | Roberts et al. |
| 8,414,576 B2 | 4/2013 | Cosmescu |
| 8,551,049 B2 | 10/2013 | Ott et al. |
| 8,551,050 B2 | 10/2013 | Ott et al. |
| 8,585,646 B2 | 11/2013 | Lloyd et al. |
| 8,608,715 B2 | 12/2013 | Roberts et al. |
| 2003/0139767 A1 | 7/2003 | Jespersen |
| 2005/0096605 A1* | 5/2005 | Green et al. ............. 604/246 |
| 2009/0221963 A1* | 9/2009 | Lloyd et al. ............. 604/119 |
| 2010/0286484 A1 | 11/2010 | Stellon et al. |
| 2011/0028891 A1 | 2/2011 | Okoniewski |

\* cited by examiner

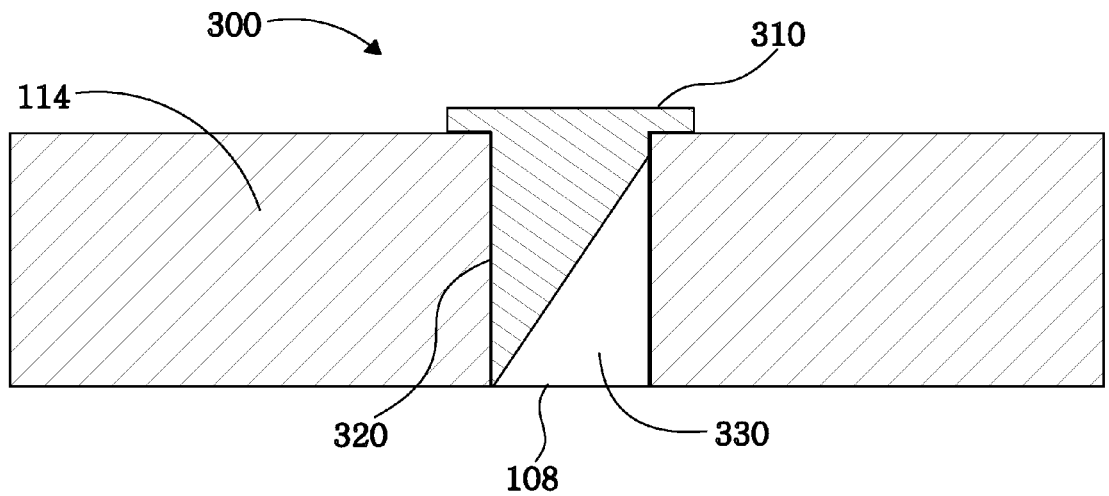
Fig. 3b
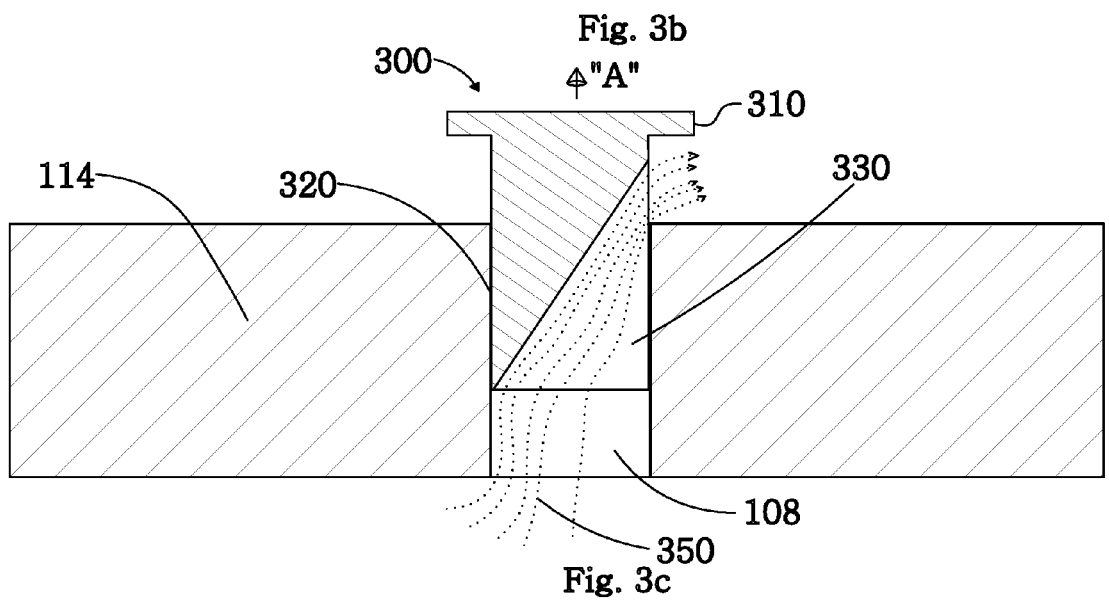

SMOKE VENT FOR ACCESS PORT DEVICE

BACKGROUND

1. Technical Field

The present disclosure relates to an apparatus and method for accessing a body cavity. More particularly, the present disclosure relates to a surgical device including an access port assembly having at least one flow regulator or smoke vent.

2. Background of Related Art

Today, many surgical procedures are performed through small incisions in the skin, as compared to the larger incisions typically required in traditional procedures, in an effort to reduce both trauma to the patient and recovery time. Generally, such procedures are referred to as "endoscopic," unless performed on the patient's abdomen, in which case the procedure is referred to as "laparoscopic." Throughout the present disclosure, the term "minimally invasive" should be understood to encompass both endoscopic and laparoscopic procedures.

During a typical minimally invasive procedure, surgical objects, such as surgical access devices, e.g., trocar and cannula assemblies, or endoscopes, are inserted into the patient's body through the incision in tissue. In general, prior to the introduction of the surgical object into the patient's body, insufflation gasses are used to enlarge the area surrounding the target surgical site to create a larger, more accessible work area. Accordingly, the maintenance of a substantially fluid-tight seal is desirable so as to prevent the escape of the insufflation gases and the deflation or collapse of the enlarged surgical site.

To this end, various valves and seals are used during the course of minimally invasive procedures and are widely known in the art. However, a continuing need exists for a seal anchor member that may be inserted directly into the incision in tissue and that may accommodate a variety of surgical objects while maintaining the integrity of an insufflated workspace.

Further, the insufflation gases may become contaminated in the course of a surgery by the incidental byproducts of a procedure such as smoke or moisture. If the contaminated insufflation gases are released from the patient's body into the extra-corporeal environment, i.e., the operating room, the contaminated insufflation gases may then interfere with the surgeon's line of sight as well as contaminate the operating environment, in turn, adversely affecting the normal operation of the surgical procedure. Additionally, the release of the contaminated insufflation gasses is an uncontrolled/inadvertent release.

SUMMARY

Accordingly, an improved access port device is provided. The access port device includes a tubular member having a proximal end and a distal end with at least one lumen extending therethrough, a first ring secured at the proximal end of the tubular member and a second ring secured at the distal end of the tubular member. The access port device further includes a flow regulator disposed on a top portion of the at least one lumen, the flow regulator having a head portion and a body portion, the body portion extending asymmetrically downward to form a substantially triangular opening for regulating an output rate of insufflation gasses from a surgical site.

The flow regulator is configured to retain the insufflation gasses from the surgical site when the head portion of the flow regulator engages the top portion of the at least one lumen. The flow regulator is configured to release the insufflation gasses from the surgical site when the head portion of the flow regulator is moved away from the top portion of the at least one lumen.

In another exemplary embodiment, the at least one access port includes a plurality of lumens, at least one of the plurality of lumens configured to allow surgical instruments to traverse therethrough.

In another exemplary embodiment, the substantially triangular opening is a dynamically adjustable opening. In other words, a leak rate of the insufflation gasses is related to a depth at which the flow regulator is inserted into the at least one lumen. Stated otherwise, the substantially triangular opening selectively regulates flow of the insufflation gasses from the surgical site.

The flow regulator may be manually operated or may be electrically operated. Additionally, the flow regulator may be formed from a flexible material.

In another exemplary embodiment, the first ring is configured to be received external of tissue and the second ring is configured to be received within a body cavity. The tubular member is configured to be tapered in a first position to facilitate insertion through tissue and is configured to define a substantially hour-glass shape in a second position.

In another exemplary embodiment, an improved surgical instrument assembly is provided. The surgical instrument assembly includes an access port having a tubular member with a first ring secured at a proximal end and a second ring secured at a distal end thereof, the tubular member including a plurality of channels extending therethrough and a smoke vent operatively associated with at least one channel of the plurality of channels, the smoke vent slidably engaging the at least one channel for regulating an output rate of smoke from a surgical site, the smoke vent including a fluctuating width opening.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 3B is a side view of the flow regulator of FIG. 3A positioned within a lumen of the access port device, the flow regulator fully inserted within the lumen, in accordance with the present disclosure;

FIG. 3C is a side view of the flow regulator of FIG. 3A positioned within a lumen of the access port device, the flow regulator partially removed from the lumen to allow a portion of the insufflation gasses to escape, in accordance with the present disclosure;

DETAILED DESCRIPTION

Figure 1:
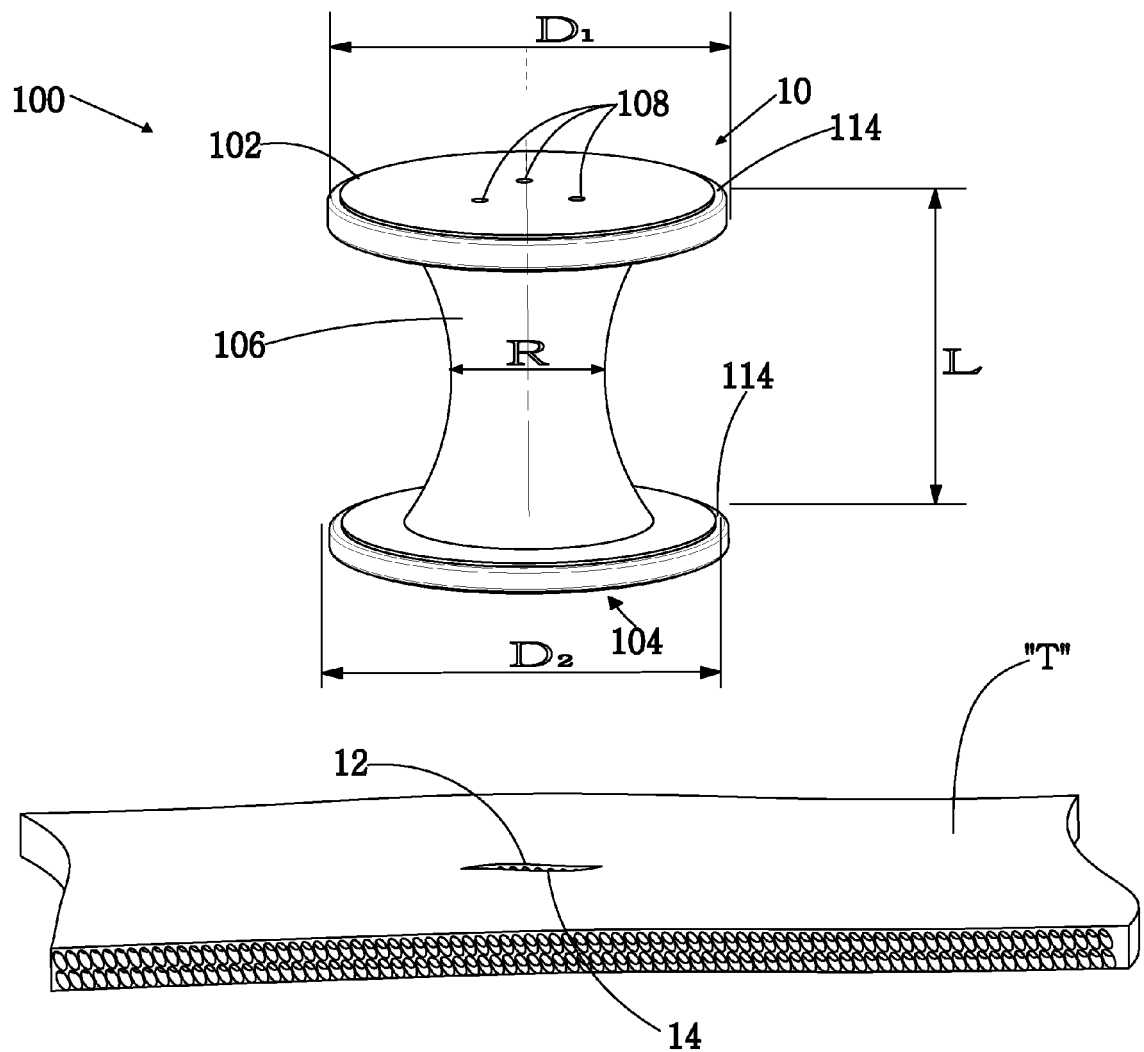
FIG. 1 is a front perspective view of a surgical apparatus in accordance with the present disclosure shown in an expanded condition illustrating a seal anchor member positioned relative to the tissue.

The access ports of the present disclosure, either alone or in combination with a cannula assembly, provide a substantially fluid-tight seal between a body cavity of a patient and the outside atmosphere. The access ports, or seal assemblies, of the present disclosure are configured to receive surgical instruments and/or flow regulators of varying diameter. Various surgical procedures contemplated include laparoscopic, arthroscopic surgical procedures, and minimally invasive surgical procedures.

The access ports of the present disclosure contemplate the introduction of various types of instrumentation adapted for insertion through a trocar and/or cannula assembly while maintaining a substantially fluid-tight interface about the instrument to help preserve the atmospheric integrity of a surgical procedure from gas and/or fluid leakage. Examples of instrumentation include, but are not limited to, clip appliers, graspers, dissectors, retractors, staplers, laser probes, photographic devices, endoscopes and laparoscopes, tubes, and the like. Such instruments will collectively be referred to as "instruments" or "instrumentation."

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user.

While the use of the access assembly is often described herein as engaging an incision, it should be recognized that this is merely exemplary and is not intended to limit the use of the assembly in any way, but rather it should be recognized that the present disclosure is intended to be useable in all instances in situations in which the access assembly engages an incision, a naturally occurring orifice, or any other suitable opening. The port is usable through an incision or through a naturally occurring orifice. A suitable example is disclosed in commonly assigned application Ser. No. 12/244,024.

Referring to FIGS. 1-4B, a surgical apparatus 10 for use in a surgical procedure, e.g., a minimally invasive procedure is illustrated. Surgical apparatus 10 includes seal anchor member 100 (or access assembly or access port or access port device) having respective trailing (or proximal) and leading (or distal) ends or rings 102, 104 and an intermediate portion 106 (e.g., a tubular member) disposed between the trailing and leading ends 102, 104. Seal anchor member 100 includes one or more lumens or channels 108 that extend longitudinally between trailing and leading ends 102, 104, respectively, and through seal anchor member 100.

Seal anchor member 100 is preferably formed from a suitable foam material having sufficient compliance to form a seal about one or more surgical objects (e.g., instrument 200, see FIG. 2), and also establish a sealing relation with the tissue, "T."

Proximal end 102 of seal anchor member 100 defines a first diameter $D_1$ and distal end 104 defines a second diameter $D_2$. In one embodiment of seal anchor member 100, the respective first and second diameters $D_1$, $D_2$ of the proximal and distal ends 102, 104 are substantially equivalent, as seen in FIG. 1, although an embodiment of seal anchor member 100 in which diameters $D_1$, $D_2$ are different is also within the scope of the present disclosure. As depicted in FIG. 1, proximal and distal ends 102, 104 define substantially planar surfaces. However, embodiments are also contemplated herein in which either or both of proximal and distal ends 102, 104, respectively, define surfaces that are substantially arcuate to assist in the insertion of seal anchor member 100 within a tissue tract 12 defined by tissue surfaces 14 and formed in tissue "T," e.g., an incision or natural orifice, as discussed in further detail below.

Intermediate portion 106 defines a radial dimension "R" and extends longitudinally between proximal and distal ends 102, 104, respectively, to define an axial dimension or length "L." The radial dimension "R" of intermediate portion 106 varies along the axial dimension, or length, "L" thereof. Accordingly, seal anchor member 100 defines a cross-sectional dimension that varies along its length "L," which facilitates the anchoring of seal anchor member 100 within tissue "T," as discussed in further detail below. However, an embodiment of seal anchor member 100 in which the radial dimension "R" remains substantially uniform along the axial dimension "L" thereof is also within the scope of the present disclosure.

The radial dimension "R" of intermediate portion 106 is appreciably less than the respective diameters $D_1$, $D_2$ of proximal and distal ends 102, 104 such that seal anchor member 100 defines an "hour-glass" shape or configuration to assist in anchoring seal anchor member 100 within tissue "T," as discussed in further detail below. However, in an alternate embodiment, the radial dimension "R" of intermediate portion 106 may be substantially equivalent to the respective diameters $D_1$, $D_2$ of proximal and distal ends 102, 104. In cross section, intermediate portion 106 may exhibit any suitable configuration, e.g., substantially circular, oval or oblong.

Referring now to FIGS. 1, 2, and 4A-4B, seal anchor member 100 is adapted to transition from an expanded condition to a compressed condition so as to facilitate the insertion and securement thereof within tissue tract 12 in tissue "T." In the expanded condition, seal anchor member 100 is at rest and the respective radial dimensions $D_1$, $D_2$ of the proximal and distal ends 102, 104 of seal anchor member 100, as well as the radial dimension R of the intermediate portion 106 are such that the seal anchor member 100 cannot be inserted within tissue tract 12. However, in the compressed condition, proximal and distal ends 102, 104 of seal anchor member 100, as well as intermediate portion 106 are dimensioned for insertion into tissue tract 12.

Seal anchor member 100 may be formed of a biocompatible compressible material that facilitates the resilient, reciprocal transitioning of seal anchor member 100 between the expanded and compressed conditions thereof. In one embodiment, the compressible material is a "memory" foam. An external force may be applied to seal anchor member 100 to cause the seal anchor member 100 to assume the compressed condition. The external force may be directed inwardly and when seal anchor member 100 is subjected thereto, e.g., when seal anchor member 100 is squeezed, seal anchor member 100 undergoes an appreciable measure of deformation, thereby transitioning into the compressed condition.

Referring again to FIG. 1, one or more positioning members 114 may be associated with either or both of trailing (or proximal) end 102 and distal (or leading) end 104 of seal anchor member 100. Positioning members 114 may be composed of any suitable biocompatible material that is at least semi-resilient such that positioning members 114 may be resiliently deformed and may exhibit any suitable configuration, e.g., substantially annular or oval.

Figure 2:
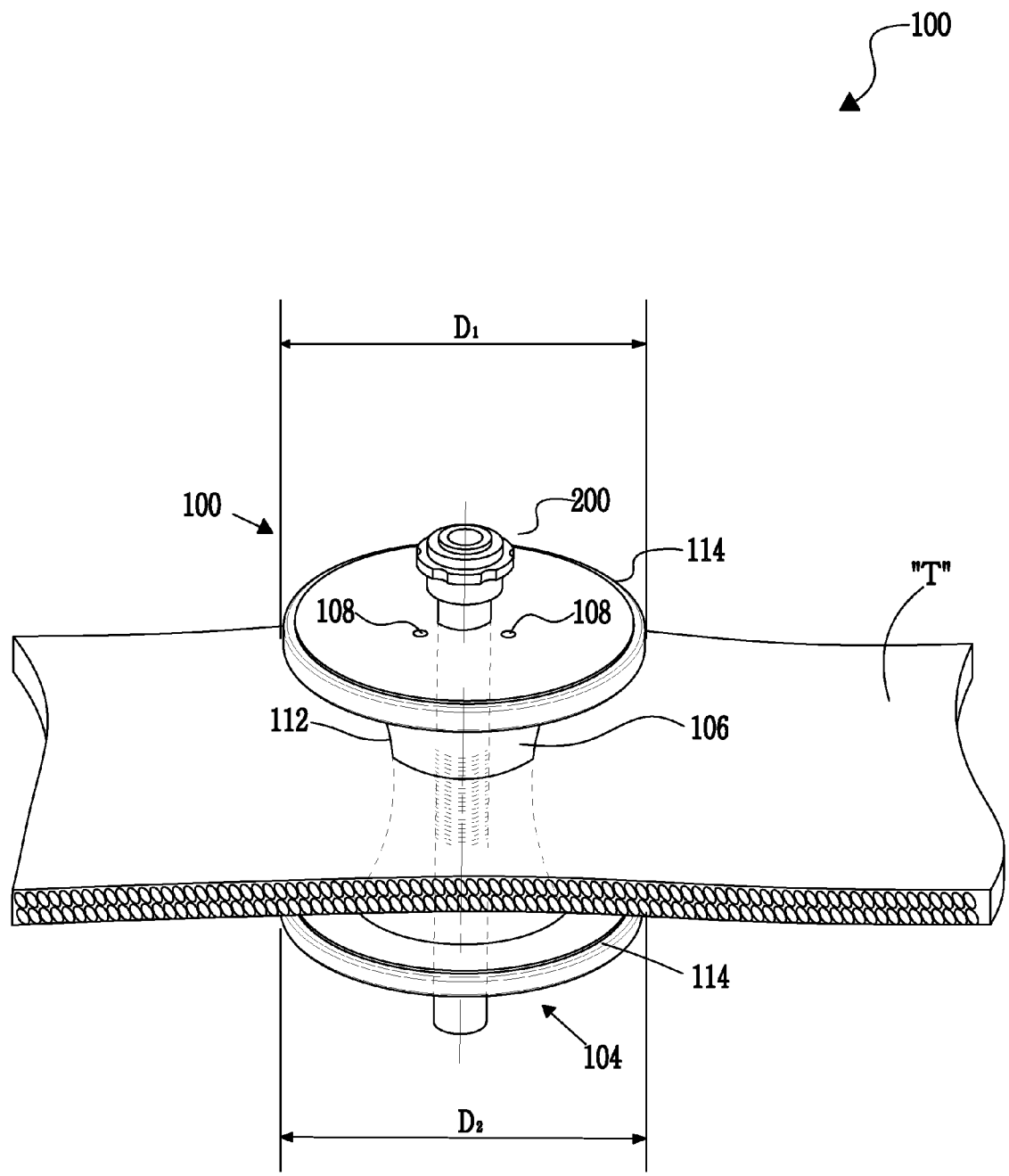
FIG. 2 is a front perspective view of the seal anchor member shown in the expanded condition and subsequent to its insertion into the incision, in accordance with the present disclosure.

Prior to the insertion of seal anchor member 100, positioning members 114 are deformed in conjunction with the respective proximal and distal ends 102, 104 of seal anchor member 100 to facilitate the advancement thereof through tissue tract 12 (see FIG. 2). Subsequent to the insertion of seal anchor member 100 within tissue tract 12, the resilient nature of positioning members 114 allows positioning members to return to their normal, substantially annular configuration, thereby aiding in the expansion of either or both of the respective proximal and distal ends 102, 104 and facilitating the transition of seal anchor member 100 from its compressed condition to its expanded condition. Positioning members 114 also may engage the walls defining the body cavity to further facilitate securement of seal anchor member 100 within the body tissue. For example, positioning member 114 at leading end 104 may engage the internal peritoneal wall and positioning member 114 adjacent trailing end 102 may engage the outer epidermal tissue adjacent the incision 12 within tissue "T." In another embodiment of seal anchor member 100, one or more additional positioning members 114 may be associated with intermediate portion 106.

In use, the peritoneal cavity (not shown) is insufflated with a suitable biocompatible gas such as, e.g., $CO_2$ gas, such that the cavity wall is raised and lifted away from the internal organs and tissue housed therein, providing greater access thereto. The insufflation may be performed with an insufflation needle or similar device, as is conventional in the art. Either prior or subsequent to insufflation, a tissue tract 12 is created in tissue "T," the dimensions of which may be varied dependent upon the nature of the procedure.

Prior to the insertion of seal anchor member 100 within tissue tract 12, seal anchor member 100 is in its expanded condition in which the dimensions thereof prohibit the insertion of seal anchor member 100 into tissue tract 12. To facilitate insertion, the clinician transitions seal anchor member 100 into the compressed condition by applying a force thereto, e.g., by squeezing seal anchor member 100. As best depicted in FIG. 2, subsequent to its insertion, distal end 104, positioning member 114 and at least a section 112 of intermediate portion 106 are disposed beneath the tissue "T." Seal anchor member 100 is caused to transition from the compressed condition to the expanded condition by removing force therefrom.

Figure 4A:
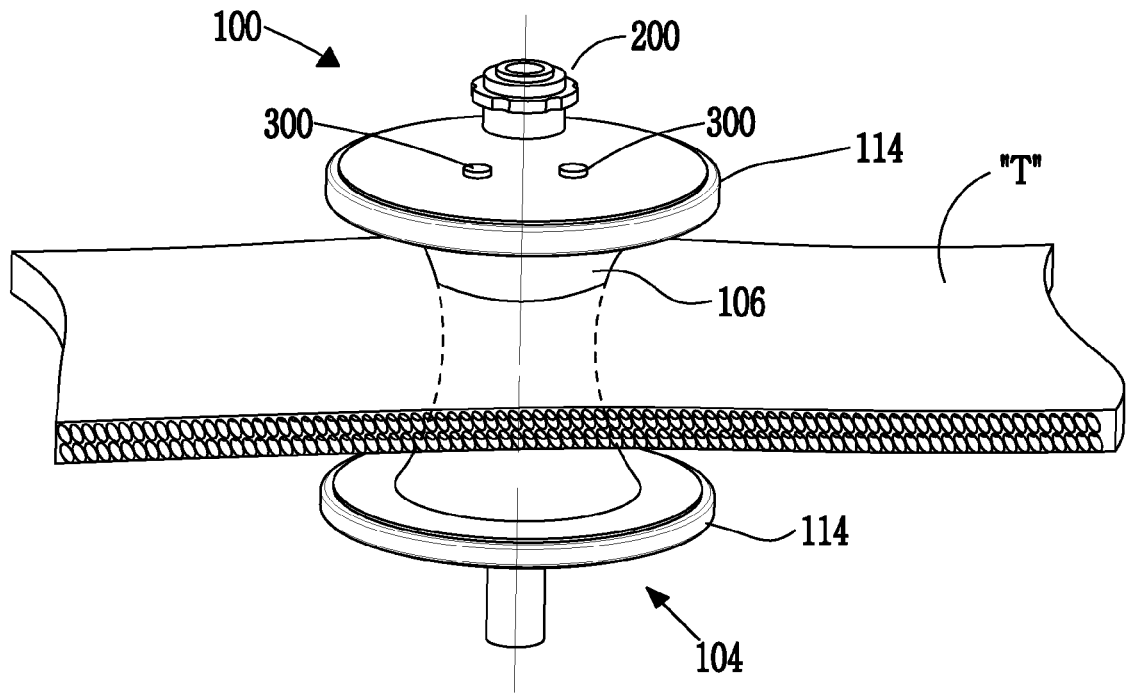
FIG. 4A is a front perspective view of the flow regulator shown fully inserted into the top portion of the access port device, in accordance with the present disclosure.
Figure 4B:
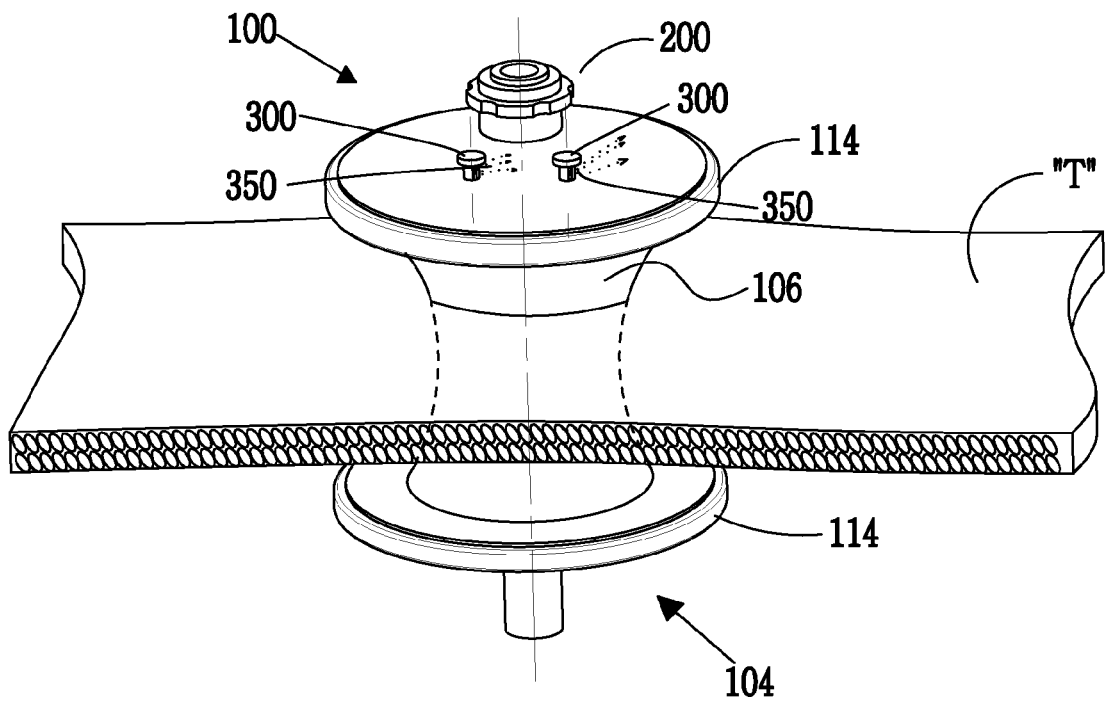
FIG. 4B is a front perspective view of the flow regulator shown partially inserted into the top portion of the access port device such that insufflation gasses escape, in accordance with the present disclosure.

After successfully anchoring seal anchor member 100 within the patient's tissue "T," one or more surgical objects may be inserted through lumens or channels 108. FIGS. 2 and 4A-4B illustrate a surgical object 200 introduced through one of lumens or channels 108. As previously discussed, prior to the insertion of surgical object 200, lumen or channel 108 is in its first state in which lumen or channel 108 defines an initial dimension. Accordingly, prior to the escape of insufflation gas through lumen or channel 108, the absence of surgical object is minimal, thereby preserving the integrity of the insufflated workspace.

Additionally, one or more flow regulators or smoke vents are inserted into the seal anchor member 100, as described with reference to FIGS. 3A-3E.

FIGS. 3A-3E illustrate a flow regulator 300 (or smoke vent 300) having a head portion 310 and a body portion 320. The body portion includes an opening 330. The opening 330 may be a substantially triangular opening. The substantially triangular opening 330 may be dynamically adjustable, as described below. The substantially triangular opening 330 may allow a surgeon to selectively regulate flow of the insufflation gasses from the surgical site. It is noted that the opening 330 may take the form of any shape or size of symmetrical or asymmetrical proportions based on user design and/or preference. In some situations other shapes may be preferred, and are certainly in keeping with the present disclosure. These shapes may include, but are not limited to, triangles, squares or other rectangles, hexagons, circles, and so one, as may be useful or desired for a particular procedure.

In FIG. 3B, the flow regulator 300 is shown fully inserted into a lumen or channel 108 of positioning member 114 of the seal anchor member 100. In the fully inserted position, the entire opening 330 is embedded within the lumen or channel 108, such that insufflation gasses do not escape from the surgical site. Thus, in operation, the flow regulator 300 is configured to retain the insufflation gasses 350 (see FIG. 3C) from the surgical site when the head portion 310 of the flow regulator 300 engages the top portion of the at least one lumen or channel 108.

In FIG. 3C, a force "A" is applied to the flow regulator 300, such that flow regulator 300 is partially removed from the lumen or channel 108. As such, a small portion of insufflation gasses 350 escape from the surgical site. Additionally, only a small portion of the opening 330 is exposed in FIG. 3C. For example, only one corner of the triangular opening 330 is exposed to allow a minor amount of insufflation gasses to escape. Additionally, the triangular opening 330 controls the flow rate out of the insufflated space.

Figure 3A:
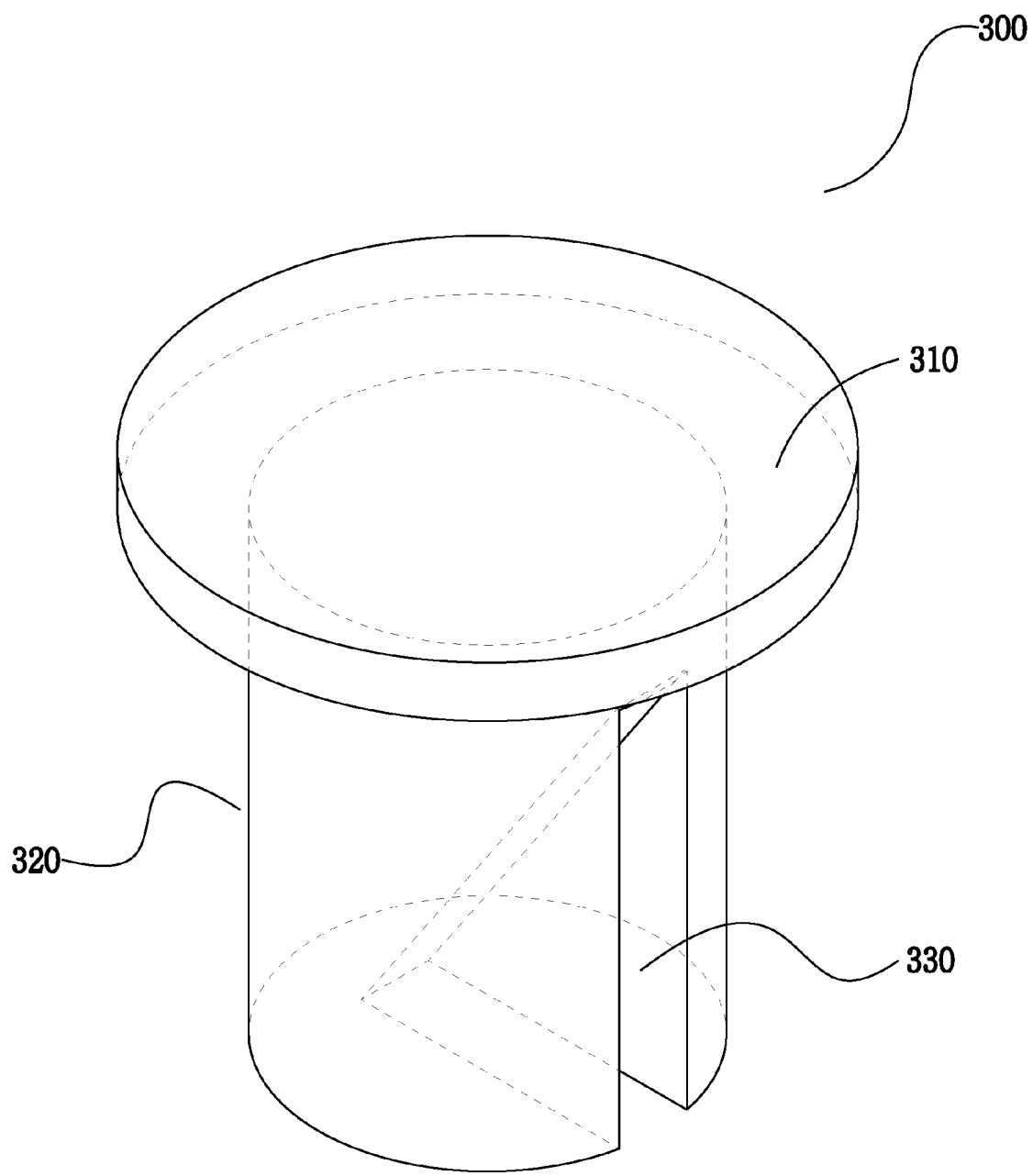
FIG. 3A is a perspective view of a flow regulator, in accordance with the present disclosure.
Figure 3D:
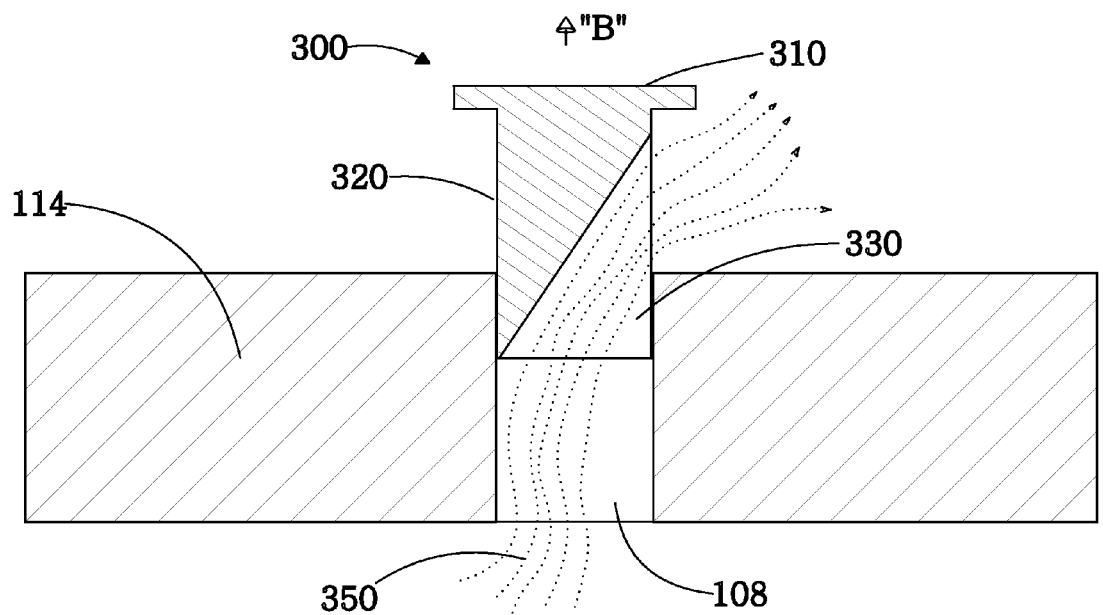
FIG. 3D is a side view of the flow regulator of FIG. 3A positioned within a lumen of the access port device, the flow regulator half-way removed from the lumen to allow more insufflation gasses to escape, in accordance with the present disclosure.

In FIG. 3D, a user applies an additional force "B" to pull the flow regulator 300 further out of the lumen or channel 108. In this instance, the flow regulator 300 has been pulled about half-way out in order to allow additional insufflation gasses 350 to be removed from the surgical site (increased flow rate), in comparison to the insufflation gasses escaping in FIG. 3C. Thus, in operation, the flow regulator 300 is configured to selectively and dynamically release the insufflation gasses 350 from the surgical site when the head portion 310 of the flow regulator 300 is forced away from the top portion of the at least one lumen or channel 108. Additionally, the triangular opening 330 controls the flow rate out of the insufflated space.

Figure 3E:
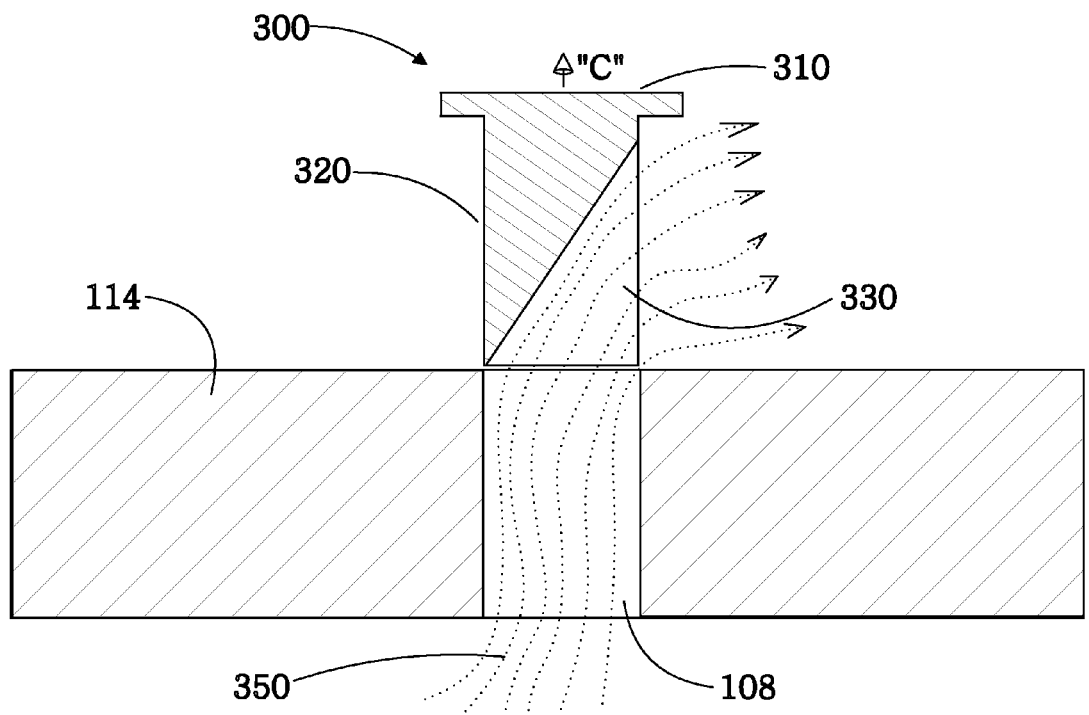
FIG. 3E is a side view of the flow regulator of FIG. 3A with the flow regulator fully removed from the lumen to allow all the insufflation gasses to escape, in accordance with the present disclosure.

In FIG. 3E, a user applies an additional force "C" to pull the flow regulator 300 further out of the lumen or channel 108, such that the entire opening 330 is exposed. In this instance, the flow regulator 300 has been pulled entirely out in order to allow all the insufflation gasses 350 to be removed from the surgical site (maximum flow rate). In other words, the entire substantially triangular opening 330 is exposed. Thus, in operation, the flow regulator 300 is configured to release the insufflation gasses 350 from the surgical site when the head portion 310 of the flow regulator 300 is forced away from the top portion of the at least one lumen or channel 108. Additionally, the triangular opening 330 controls the flow rate out of the insufflated space.

As a result, a user is permitted to selectively and dynamically adjust the opening 330 in accordance with how much insufflation gasses 350 (or flow rate of gasses 350) are desired to be removed from the surgical site. In other words, a leak rate of the insufflation gasses 350 is related to a depth at which the flow regulator 300 is inserted into or removed from the at least one lumen or channel 108. Stated otherwise, a smoke vent 300 may be operatively associated with at least one channel 108 of the plurality of channels 108, the smoke vent 300 slidably engaging the at least one channel 108 for regulating an output rate of smoke 350 from a surgical site, the smoke vent 300 including a fluctuating width opening 330.

Moreover, the flow regulator 300 may be manually operated or may be electronically operated. For example, some type of wireless control mechanism may be associated with the flow regulator 300 in order to actuate its movement. The flow regulator 300 may also be constructed from a flexible material, such as a foam material.

FIG. 4A is a front perspective view of the flow regulator 300 shown fully inserted into the top portion of the access port device, whereas FIG. 4B is a front perspective view of the flow regulator 300 shown partially inserted into the top portion of the access port device such that insufflation gasses escape. FIGS. 4A-4B illustrate the flow regulator 300 of FIGS. 3A-3E fully and partially inserted into a channel or lumen 108, and its interaction with the seal anchor member 100.

Therefore, in summary an evacuation method is disclosed for removing laser smoke or electrocautery smoke from an operation site in a patient cavity during, for example, laparoscopy. The method comprises inserting a laparoscopic access port device having a smoke vent or flow regulator on a top portion of a surgical instrument assembly. Laparoscopic surgery may then be performed. The smoke vent or flow regulator is selectively and dynamically adjusted to provide either a continuous or discontinuous suction for withdrawal of smoke and other contaminants from the patient cavity. A smoke-free environment for surgeons and patient is thus provided.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. An access port device, comprising:
   a tubular member having a proximal end and a distal end with at least one lumen extending therethrough;
   a first ring secured at the proximal end of the tubular member;
   a second ring secured at the distal end of the tubular member; and
   a flow regulator disposed within the at least one lumen, the flow regulator having a head portion and a body portion, the body portion extending asymmetrically downward to form a substantially triangular opening for regulating an output rate of insufflation gasses from a surgical site.

2. The access port device according to claim 1, wherein the flow regulator is configured to retain the insufflation gasses within the surgical site when the head portion of the flow regulator contacts a proximal end of the at least one lumen.

3. The access port device according to claim 1, wherein the flow regulator is configured to release the insufflation gasses from the surgical site when the head portion of the flow regulator is moved away from a proximal end of the at least one lumen.

4. The access port device according to claim 1, wherein the at least one lumen includes a plurality of lumens, at least one lumen of the plurality of lumens configured to allow surgical instruments to traverse therethrough.

5. The access port device according to claim 1, wherein the substantially triangular opening is a dynamically adjustable opening.

6. The access port device according to claim 1, wherein a leak rate of the insufflation gasses is related to a depth at which the flow regulator is inserted into the at least one lumen.

7. The access port device according to claim 1, wherein the substantially triangular opening selectively regulates flow of the insufflation gasses from the surgical site.

8. The access port device according to claim 1, wherein the flow regulator is manually operated.

9. The access port device according to claim 1, wherein the flow regulator is formed from a flexible material.

10. The access port device according to claim 1, wherein the first ring is configured to be received external of tissue.

11. The access port device according to claim 1, wherein the second ring is configured to be received within a body cavity.

12. The access port device according to claim 1, wherein the tubular member is configured to be tapered in a first position to facilitate insertion through tissue and is configured to define a substantially hour-glass shape in a second position.

13. A surgical instrument assembly, comprising:
   an access port having a tubular member with a first ring secured at a proximal end and a second ring secured at a distal end thereof, the tubular member including a plurality of channels extending therethrough; and
   a smoke vent operatively associated with at least one channel of the plurality of channels, the smoke vent slidably displaced within the at least one channel for regulating an output rate of smoke from a surgical site, the smoke vent including a fluctuating width opening.

14. The surgical instrument assembly according to claim 13, wherein the fluctuating width opening is a dynamically adjustable opening.

15. The surgical instrument assembly according to claim 13, wherein a leak rate of the smoke is related to a depth at which the smoke vent is inserted into the at least one channel.

16. The surgical instrument assembly according to claim 13, wherein the fluctuating width opening selectively regulates flow of the smoke from the surgical site.

17. The surgical instrument assembly according to claim 13, wherein the smoke vent is configured to retain the smoke within the surgical site when a head portion of the smoke vent engages a top portion of the at least one channel.

18. The surgical instrument assembly according to claim 13, wherein the smoke vent is configured to release the smoke from the surgical site when a head portion of the smoke vent is spaced apart from a top portion of the at least one channel.

19. The surgical instrument assembly according to claim 13, wherein the smoke vent is positioned within the at least one channel of the plurality of channels.

* * * * *